US007695192B2

(12) United States Patent
Henderson et al.

(10) Patent No.: US 7,695,192 B2
(45) Date of Patent: Apr. 13, 2010

(54) IMAGING POSITIONING SYSTEM HAVING ROBOTICALLY POSITIONED D-ARM

(76) Inventors: Toby D. Henderson, 27 Springbrook Rd., Rockford, IL (US) 61114; Niek Schreuder, 6140 W. Duvall Rd., Bloomington, IN (US) 47403

( * ) Notice: Subject to any disclaimer, the term of this patent is extended or adjusted under 35 U.S.C. 154(b) by 0 days.

(21) Appl. No.: 12/208,852

(22) Filed: Sep. 11, 2008

(65) Prior Publication Data
US 2009/0074151 A1    Mar. 19, 2009

Related U.S. Application Data

(60) Provisional application No. 60/972,078, filed on Sep. 13, 2007.

(51) Int. Cl.
*H05G 1/02* (2006.01)
(52) U.S. Cl. ...................................................... 378/198
(58) Field of Classification Search ......... 378/193–198, 378/62
See application file for complete search history.

(56) References Cited

U.S. PATENT DOCUMENTS

| | | | |
|---|---|---|---|
| 5,321,271 A | 6/1994 | Schonberg et al. | 250/492.3 |
| 5,540,649 A | 7/1996 | Bonnell et al. | 600/114 |
| 5,548,625 A | 8/1996 | Waldo, III | 378/34 |
| 5,727,554 A | 3/1998 | Kalend et al. | 600/587 |
| 5,784,431 A | 7/1998 | Kalend et al. | 378/65 |
| 6,811,313 B2 | 11/2004 | Graumann et al. | 378/196 |
| 6,869,217 B2 | 3/2005 | Rasche et al. | 378/197 |
| 6,940,941 B2* | 9/2005 | Gregerson et al. | 378/4 |
| 7,154,991 B2 | 12/2006 | Earnst et al. | 378/65 |
| 2001/0005410 A1* | 6/2001 | Rasche et al. | 378/197 |
| 2002/0181650 A1* | 12/2002 | D'Ambrosio | 378/43 |

(Continued)

FOREIGN PATENT DOCUMENTS

KR    1020060135063 A    12/2006

(Continued)

OTHER PUBLICATIONS

Anferov et al.; The expected radiation failure rate for optical encoders used in the MPRI patient positioner; (presentation) Particle Therapy Co-Operative Group Meeting - Catania, Italy; 11 pgs.; May 27-31, 2002.

(Continued)

*Primary Examiner*—Courtney Thomas
(74) *Attorney, Agent, or Firm*—Reinhart Boerner Van Deuren P.C.

(57) ABSTRACT

An imaging positioning system having a robotically positioned support structure is provided. By utilizing a robotic arm, imaging along multiple planes within a patient treatment room without having to move the patient is provided. Such a configuration allows multiple axis x-ray imaging, cone beam CT acquisitions having a dynamic field of view, and PET imaging within the treatment room. Rotation of the imaging panel on the support structure allows the imaging system to simulate a gantry rotation when a fixed beam is used for treatment. Beam line x-ray imaging is also provided by tilting the imaging panel or by moving the support structure on which the x-ray source is positioned. Laser distance scanning for collision avoidance and force torque sensing movement enhance the safety thereof. The support structure may be in the form of a ring along which the imaging components may move.

16 Claims, 13 Drawing Sheets

U.S. PATENT DOCUMENTS

| | | | |
|---|---|---|---|
| 2004/0064153 A1 | 4/2004 | Creighton, IV et al. | 607/1 |
| 2005/0187424 A1 | 8/2005 | Hambuchen et al. | 600/12 |
| 2005/0234327 A1 | 10/2005 | Saracen et al. | 600/407 |
| 2006/0050847 A1 | 3/2006 | Jaffray et al. | 378/65 |
| 2007/0230660 A1 | 10/2007 | Herrmann | 378/65 |
| 2009/0070936 A1 | 3/2009 | Henderson et al. | 5/601 |

FOREIGN PATENT DOCUMENTS

| | | |
|---|---|---|
| KR | 100695468 B1 | 3/2007 |
| WO | WO 2006/034973 A1 | 4/2006 |

OTHER PUBLICATIONS

Kats et al.; A planar magnetooptical system for the irradiation of a lying patient with a proton beam from various directions; Instruments and Experimental Techniques; vol. 39; No. 1; pp. 127-134; 1996.

Kats, M.; Planar system replacing gantry for protons and carbon ions beams transportation; Proceedings of the 6th European Particle Accelerator Conference (EPAC'98); pp. 2362-2364, 1998.

Katuin et al.; The use of industrial robot arms for high precision patient positioning; CAARI; 4 pgs.; 2002.

Schreuder et al.; Beam delivery developments; (presentation) Particle Therapy Co-Operative Group Meeting; 20 pgs.; May 14, 2003.

Schreuder et al.; IGRT methods used in patient positioning; (presentation) ORVC Fall 2005 Meeting; Indiana Univ. Cyclotron facility - Bloomington, Indiana; 26 pgs.; Nov. 5, 2005.

Schreuder et al.; MPRI operational aspects; (presentation) Particle Therapy Co-Operative Group Meeting—Bloomington, Indiana; 24 pgs.; Oct. 10-13, 2004.

Schreuder et al.; The MPRI robotic patient positioner; (presentation) Particle Therapy Co-Operative Group Meeting - Paris; 14 pgs.; Jun. 16, 2004.

Schreuder et al.; The non-orthogonal fixed beam arrangement for the second proton therapy facility at the national accelerator centre; CAARI; 4 pgs.; 1998.

Schreuder et al.; Using industrial robots for high precision patient positioning in proton radiotherapy; (presentation) RIA - Orlando, Florida; 48 pgs.; Nov. 19, 2004.

* cited by examiner

IMAGING POSITIONING SYSTEM HAVING ROBOTICALLY POSITIONED D-ARM

CROSS-REFERENCE TO RELATED PATENT APPLICATIONS

This patent application claims the benefit of U.S. Provisional Patent Application No. 60/972,078, filed Sep. 13, 2007, the teaching and disclosure of which are hereby incorporated in their entireties by reference thereto.

FIELD OF THE INVENTION

This invention generally relates to patient imaging systems, and more particularly to patient imaging systems for use in therapeutic radiation treatment operations such as proton and ion beam treatment.

BACKGROUND OF THE INVENTION

Continuing advances in medical science, and specifically in the field of radiation treatment, have allowed the development of more precise, targeted treatment options for patients with tumorous cells that results in less radiation being applied to healthy cells. However, for each of the two main types of radiation treatment, i.e. radiosurgery and radiotherapy, precise imaging of the tumor location is critical to ensure the radiation is delivered only to the target area. This is particularly important in radiosurgery because of the intense doses of radiation that are delivered to the patient are intended to destroy tumorous cells or otherwise treat the target region. While the amount of radiation delivered to a patient during radiotherapy is typically about an order of magnitude smaller than used in radiosurgery, for example to treat early stage cancers, precise delivery to the cancerous cells is still very important to minimize the negative impact on the patient. As such and for ease of understanding, the following description will use the term radiotherapy to refer to both radiosurgery and radiotherapy.

In each of these radiation treatment operations, it is necessary to determine with precision the location of the target region and surrounding critical structures relative to the reference frame of the treatment device. It is also necessary to control the position of the radiation source so that its beam can be precisely directed to the target tissue while avoiding surrounding healthy tissue, with control of propagation in and through other body structures.

To effect such beam position control, frameless stereotactic radiotherapy systems have been developed, which implement image-guided radiotherapy using a robot. An image-guided robotic system provides the requisite beam position control for accurate delivery of therapeutic radiation, while eliminating the need for rigid stereotactic frames. Such image-guided robotic systems typically include a treatment beam generator mounted onto a robot and a controller. The treatment beam generator provides precisely shaped and timed radiation beams. Using pre-treatment scan data, as well as treatment planning and delivery software, the controller acquires information regarding the pre-treatment position and orientation of the treatment target region. The patient is usually placed on a support device, such as a couch or a table. During treatment, an imaging system repeatedly measures the position and orientation of the target relative to the x-ray source. Prior to the delivery of radiation at each delivery site, the controller directs the robot to adjust the position and orientation of the treatment beam generator, in accordance with the measurements made by imaging system, so that the requisite dose of the treatment beam can be applied to the treatment target within the patient.

FIG. 1 schematically illustrates one such radiotherapy system 10 described in U.S. Pat. No. 7,154,991 B2, entitled Patient Positioning Assembly For Therapeutic Radiation System, assigned to Accuray, Inc. This system 10 includes a robot 12 having an articulated arm assembly 13, a therapeutic radiation source 14 mounted at a distal end of the articulated arm assembly 13 for selectively emitting therapeutic radiation, an x-ray imaging system and a controller 18.

The x-ray imaging system generates image data representative of one or more near real time images of the target. The x-ray imaging system includes a pair of diagnostic x-ray sources 17, and a pair of x-ray image detectors (or cameras) 21, each detector located opposite an associated one of the x-ray sources 17. A patient support device (or treatment table) 19 supports the patient during treatment, and is positioned between the two x-ray cameras 21 and their respective diagnostic x-ray sources 17.

The imaging system generates, in near real time, x-ray images showing the position and orientation of the target in a treatment coordinate frame. The controller 18 contains treatment planning and delivery software, which is responsive to pre-treatment scan data CT (and/or MRI data and/or PET data and/or ultrasound scan data) and user input, to generate a treatment plan consisting of a succession of desired beam paths, each having an associated dose rate and duration at each of a fixed set of nodes.

Prior to performing a treatment on a patient, the patient's position and orientation within the frame of reference established by the x-ray imaging system must be adjusted to match the position and orientation that the patient had within the frame of reference of the CT (or MRI or PET) scanner that provided the images used for planning the treatment. It is desirable that this patient alignment be performed to within tenths of a millimeter and tenths of a degree for all six degrees of freedom.

Unfortunately, with such a mounted imaging system 10, the imaging views that are able to be taken are limited in orientation. Further, since the imaging system 10 is mounted, requiring two x-ray sources 17 and two cameras 21, the patient must be moved between the cameras 21 to image different parts or areas of the body. Any such movement of the table 19 once set up runs the risk of disturbing the alignment, i.e. patient's position and orientation, which will then need to be re-confirmed and set-up before further treatment is begun. Still further, such an imaging system 10 places constraints on the treatment envelope within the treatment room so as to avoid collisions between the table 19 and the cameras 21. These camera structures also take up, and therefore limit, the available space within the treatment room, obstructing free movement of the technician or other medical personnel when in the treatment room.

Additional radiotherapy systems are illustrated in U.S. Patent Publication Number 2007/0230660, entitled Medical Radiotherapy Assembly, by Klaus Herrmann. The '660 publication illustrates a first system where the imaging system is mounted to the therapeutic radiation source such that the x-ray source and x-ray detector of the imaging system rotate only angularly about a longitudinal axis defined by the particle beam of the therapeutic radiation source.

Again, unfortunately, with this mounted imaging system arrangement, the imaging views that are able to be taken are limited in orientation to being angularly positioned about the particle beam. Therefore, it is impossible in this system to align the imaging system, namely the x-ray source and x-ray detector, with the direction of particle beam.

A second system is disclosed in the '660 publication that includes an imaging system including an x-ray source and x-ray detector mounted to a support arm that is C-or U-shaped. This C- or U-shaped allows the support arm to be open on one side. This support arm is mounted to a six axes robot.

While this arrangement permits some improved positioning of the imaging system over the previous systems, the imaging system of this radiotherapy system (i.e. both he x-ray source and the x-ray detector) the x-ray detector of the imaging system cannot be used to help align or check alignment of the particle beam relative to the target area. Particularly, the x-ray source of the imaging system would be in the way of a particle beam line x-ray source of the therapeutic radiation source.

Instead, if the alignment of the particle beam is to be checked prior to therapy, a secondary independent x-ray detector must be positioned in place of the x-ray detector of the imaging system to cooperate with a particle beam line x-ray image prior to initiating the therapy of the patient. Again, this unfortunately, requires additional set-up of another imaging device which inherently imports potential error in the alignment of the particle beam.

Further, to adjust the orientation of the imaging system relative to a patient, the entire support arm and robot must be moved relative about the patient. Unfortunately, rotating the entire support arm from the mounting point requires overcoming substantial rotational inertia due to the size and weight of the support arm and the moment arm created by offsetting the x-ray detector and x-ray source from the point of rotation of the support arm.

BRIEF SUMMARY OF THE INVENTION

Embodiments of the present invention provide a new and improved imaging positioning system. More particularly, embodiments of the present invention provide new and improved imaging positioning systems that overcome one or more of the above-described problems existing with current imaging systems utilized for therapeutic radiation treatment operations. More particularly, embodiments of the present invention provide new and improved imaging positioning systems having a robotically positioned support structure for carrying and position imaging equipment.

In one embodiment, the support structure is a D-arm that houses an x-ray source on one leg and a radiographic imaging panel on the other. In another embodiment the D-arm houses a cone beam CT source on one leg and an imaging panel on the other. Still other embodiments of the present invention utilize positron emission tomography (PET) cameras mounted on each of the legs of the D-arm to allow PET imaging. Still other embodiments of the present invention utilize a combination of these imaging technologies to satisfy the imaging requirements of the therapeutic radiation treatment operations used therewith.

In one embodiment of the present invention, the imaging system utilizes a selectively compliant articulated robot arm (SCARA) type robot that provides five rotations and one linear translation axis. To maximize the available space within a treatment room, an embodiment of the present invention mounts the SCARA type robot in the ceiling of the treatment room. The SCARA type robot is then able to position the support structure so that the patient is within a volume defined by the support structure and the imaging components of the imaging equipment carried thereon. This allows imaging orientations along nearly every plane without requiring movement of the patient or the positioning table on which the patient has been secured.

For x-ray imaging, only one x-ray source and one radiographic imaging panel is required. By using a SCARA type high payload, high precision robot to position the D-arm on which the imaging equipment is mounted, very high precision and repeatable positioning of the imaging equipment is enabled. This greatly simplifies the commissioning process. As such, embodiments of the present invention may be used to acquire static x-ray images along multiple axis through the treatment room isocenter. This provides a more adaptable solution and will allow for easier integration with multiple patient alignment systems that control the positioning of the patient and the treatment beam. One such patient positioning system is described in co-pending application Ser. No. 60/972,107, filed on Sep. 13, 2007, the teachings and disclosure of which are hereby incorporated in their entireties by reference thereto.

In an alternate embodiment of the present invention, cone beam CT (CBCT) acquisition is made possible by dynamically rotating the D-arm about the patient in multiple planes. Indeed, in an embodiment of the present invention the center of rotation during CBCT acquisition between the source and the imaging panel is provided by the SCARA robot. As such, the technician or medical personnel is able to define a point of rotation for the D-arm, which allows the technician or medical personnel to define or adjust the field of view (FOV) provided by the CBCT. If a bigger FOV is required or desired, the point of rotation of the D-arm controlled by the robot will be closer to the imaging panel, while a smaller FOV will be provided by defining a point of rotation that is farther from the imaging panel. Further, the fact that the CBCT acquisition can be done in multiple planes with an embodiment of the system of the present invention, CBCT acquisitions are now able to be performed on the patient while the patient is in the treatment position. The control of the imaging system of the present invention also allows for CBCT acquisitions with the patient positioned in a seated position. This enabled in one embodiment by positioning the D-arm to allow acquisition of CBCT in the horizontal plane.

In an embodiment of the present invention, a mechanism is provided to allow rotation of the imaging panel on the support structure about the x-ray beam axis. This allows the imaging system to simulate a gantry rotation when a fixed proton beam, that cannot rotate, is used. The classical way of using static radiographic images is to have the imaging panels in a fixed orientation with respect to the fixed reference coordinate system in the treatment room. When the patient is moved, instead of the beam (gantry), then the radiographic image obtained with the fixed panel will not align with the reference image obtained from the treatment planning system. In one embodiment of the present invention, the imaging panel is rotated about the x-ray axis to simulate the effect of a beam rotation.

In one embodiment of the present invention, the support structure is divided into separate segments or portions allow the imaging panel and x-ray source to be moved out of the same plane of the imaging panel. This allows the imaging panel on the support structure to be used for a beam line x-ray image. In another embodiment the image panel mount on the support structure includes a mechanism to allow the imaging panel itself to be tilted out of the x-ray beam axis of the x-ray source mounted on the support structure so that the imaging panel can be positioned perpendicular to the proton beam axis without the x-ray source hitting the beam delivery nozzle during beam line x-ray imaging.

In an embodiment of the present invention, an image panel mount will allow the imaging panel to tilt out of the plane of an x-ray beam axis so that the imaging panel can be positioned perpendicular to a proton beam axis without the x-ray source hitting the beam delivery nozzle. In other words, the support structure and imaging panel will be rotated relative to one another such that the image panel remains in its same location relative to a patient, while transitioning the x-ray source out of line with the previous axis that it maintained. Thus, a new x-ray source associated with the beam delivery nozzle can be aligned with the imaging panel to properly align the beam delivery nozzle relative to the target region of the patient.

To ensure that no object will collide with the support structure, one embodiment of the system of the present invention utilizes a laser distance tracking device mounted on the support structure. During use of the imaging system, the laser distance tracking device will sweep over the volume enclosed by the support structure so that it may sense the presence of any objects that come in close proximity to any mechanical part of the imaging system. This laser distance scanner is also used in an alternate embodiment to determine the patient's surface envelope for use with the imaging system, patient positioning system and treatment system's collision avoidance control algorithms.

In an embodiment of the present invention a force torque sensor is included between the robot wrist and the support structure. All motions, except for the dynamic CBCT acquisitions, will then be under force torque control. This means that none of the motions about the patient to get the support structure in position will be autonomous, i.e., the imaging positioning system will only move along the path that the technician or other medical personnel pulls it.

In further alternative embodiments, the support structure is mounted to the SCARA robot at a coupling and an imaging device is mounted to the support structure. In a preferred embodiment, an orientation of the imaging device relative to the coupling between the SCARA robot and the support structure is adjustable. This allows for further precision in the operation of the imaging positioning system and particularly positioning the imaging device relative to a target area of a patient.

In a further embodiment, the support structure is a support ring, which is a ring like structure that is preferably a continuous ring. The support ring allows for rotating the orientation of the imaging device 360 degrees about a central axis. In a preferred embodiment, the imaging device may move relative to the support ring to adjust the position of the imaging device components relative to the coupling and the SCARA robot. This arrangement greatly reduces the number of components of the overall imaging positioning system that must be moved to make some adjustments of the orientation of the imaging device.

Further yet, in some embodiments, the support ring is formed by a pair of segments or portions that are pivotally connected to one another. This allows the support ring to pivot between different pivoted states, namely a closed pivoted state where the support ring is a continuous ring and a second open pivoted state where the support ring is broken, thereby forming a mouth between the ends of the segments of the support ring. This allows the support ring to be more easily positioned about a patient. Once positioned about the patient, the support ring can be transitioned to the closed pivoted state where the support ring continuously surrounds an axis defined by the patient.

In another embodiment, the coupling between the support structure and the robotic arm is adjustable such that the orientation of the imaging device is adjustable relative to the coupling by adjusting the location of the coupling to the support structure. More particularly, in one preferred embodiment, the coupling includes a coupling plate that is moveable relative to and along the support structure.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
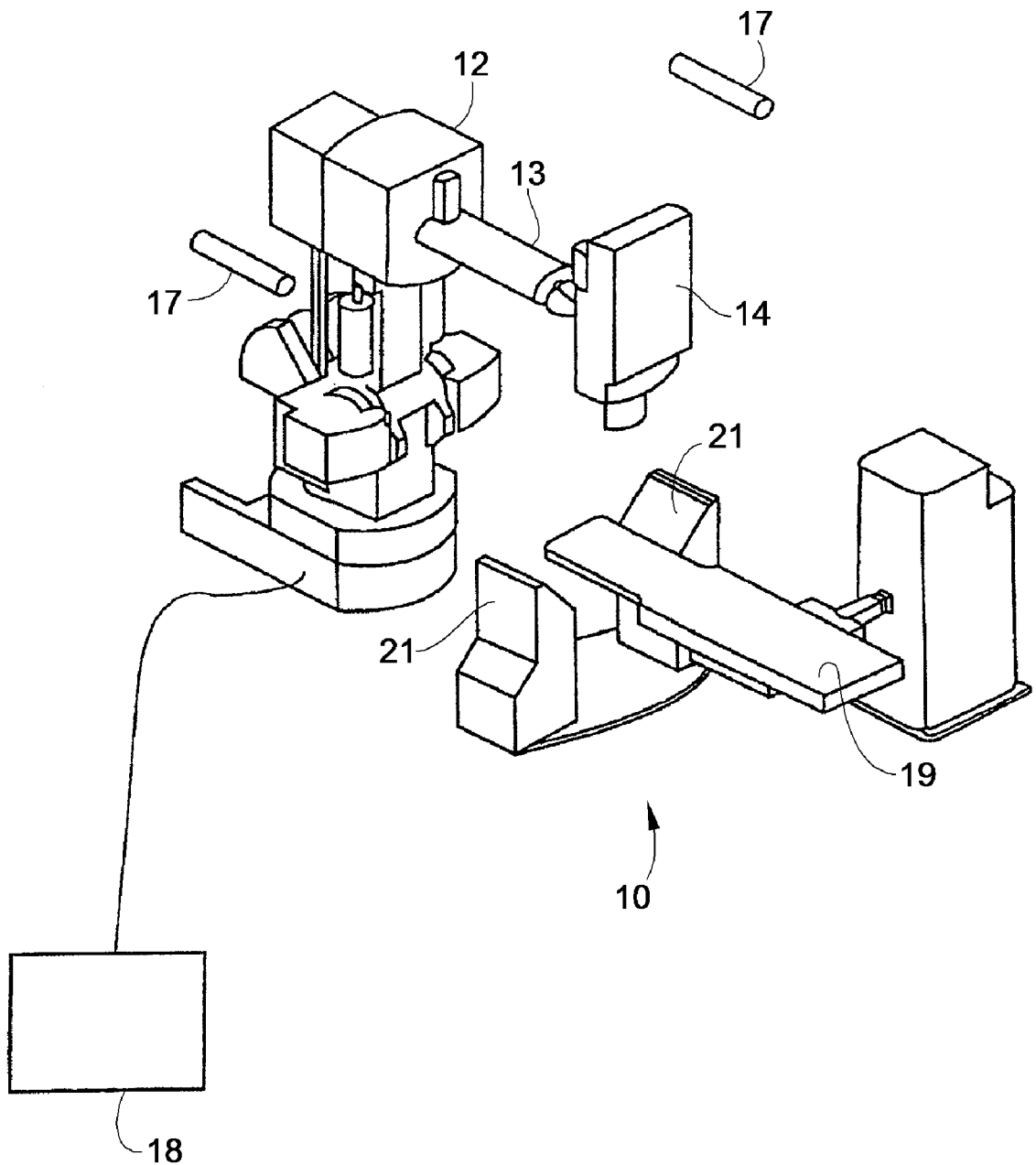
FIG. 1 schematically illustrates a frameless radiotherapy system, known in the prior art.
Figure 2:
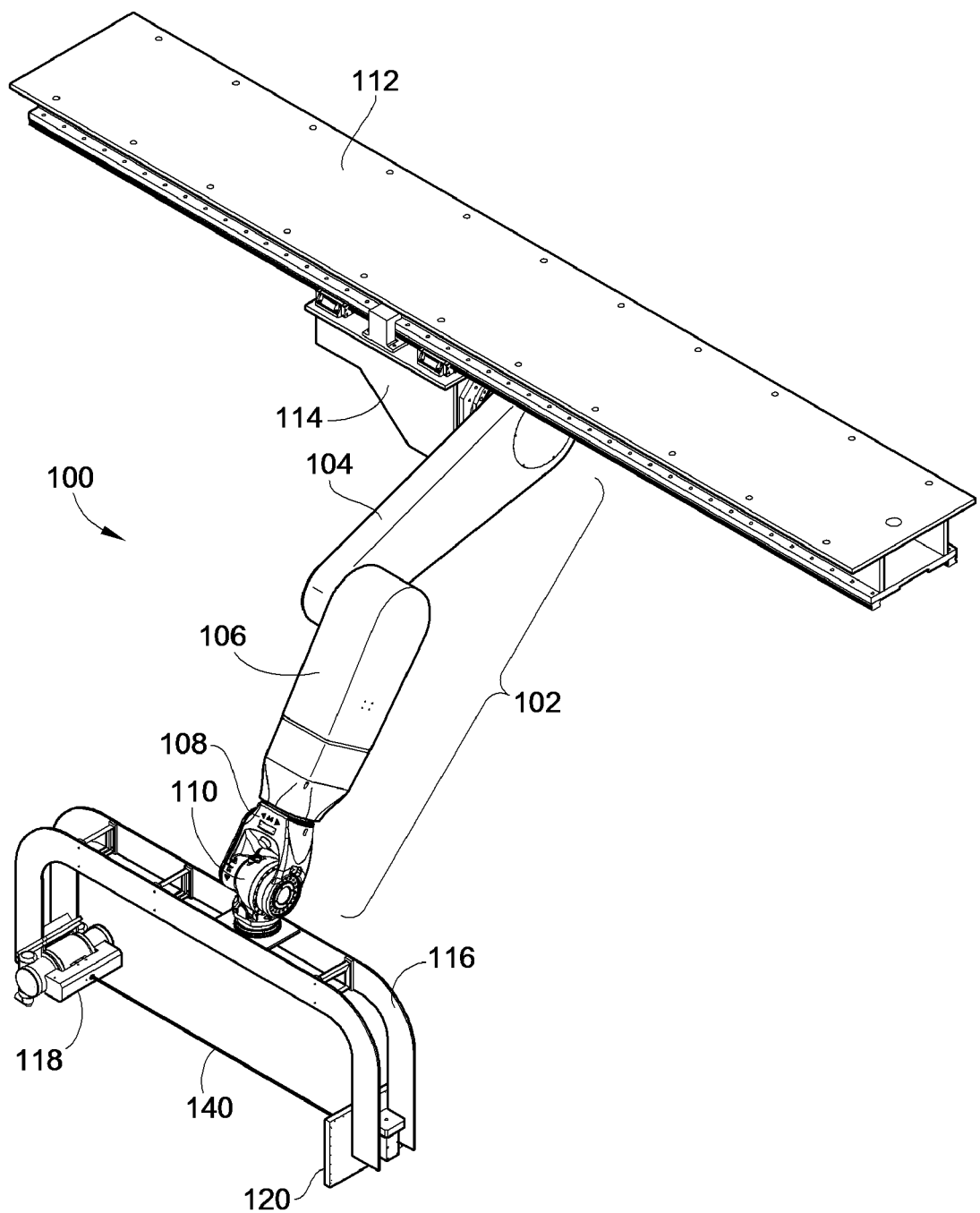
FIG. 2 is an isometric illustration of an embodiment of an imaging positioning system constructed in accordance with the teachings of the present invention.

Turning now to FIG. 2, there is illustrated an embodiment of an imaging positioning system 100 constructed in accordance with the teachings of the present invention. While the following description will describe embodiments of the imaging positioning system in relation to its use in therapeutic radiation treatment operations and facilities, those skilled in the art will recognize that such embodiments and operating environments are provided by way of example only, and not by way of limitation.

In the illustrated embodiment, the imaging positioning system 100 utilizes a selectively compliant articulated robot arm (SCARA) type robot 102 that provides five rotations and one linear translation axis. Other embodiments of the present invention may utilize a standard six axis robot. The SCARA type robot 102 of the illustrated embodiment includes an upper arm portion 104, a lower arm portion 106, a wrist portion 108 and a coupling portion 110. Linear translation is provided along a mounting track 112 by base portion 114. To maximize the available space within the treatment room of the therapeutic radiation treatment center, a preferred embodiment of the present invention installs the mounting track 112 in the ceiling so that the imaging system 100 may be moved up and out of the way when not needed so as to not inhibit the movement of any of the technicians, medical personnel, or the patient within the treatment room.

The imaging positioning system 100 utilizes a support structure in the form of a D-arm structure 116 on which the imaging equipment is mounted. In the embodiment illustrated in FIG. 2, this imaging equipment has two separate primary components shown as an x-ray source 118 and an imaging panel 120, each component is mounted to an opposed one of legs of the D-arm. Other embodiments of the present invention utilize other imaging devices to allow cone beam CT (CBCT) acquisition, positron emission tomography (PET) imaging, etc. as will be discussed more fully below. Still further, other embodiments of the present invention utilize multiple imaging device technologies mounted on the D-arm structure 116 to provide multiple types of imaging, for example, both an x-ray source 118 and imaging panel 120 and a pair of PET cameras to allow PET scanning during the treatment operation.

Figure 3:
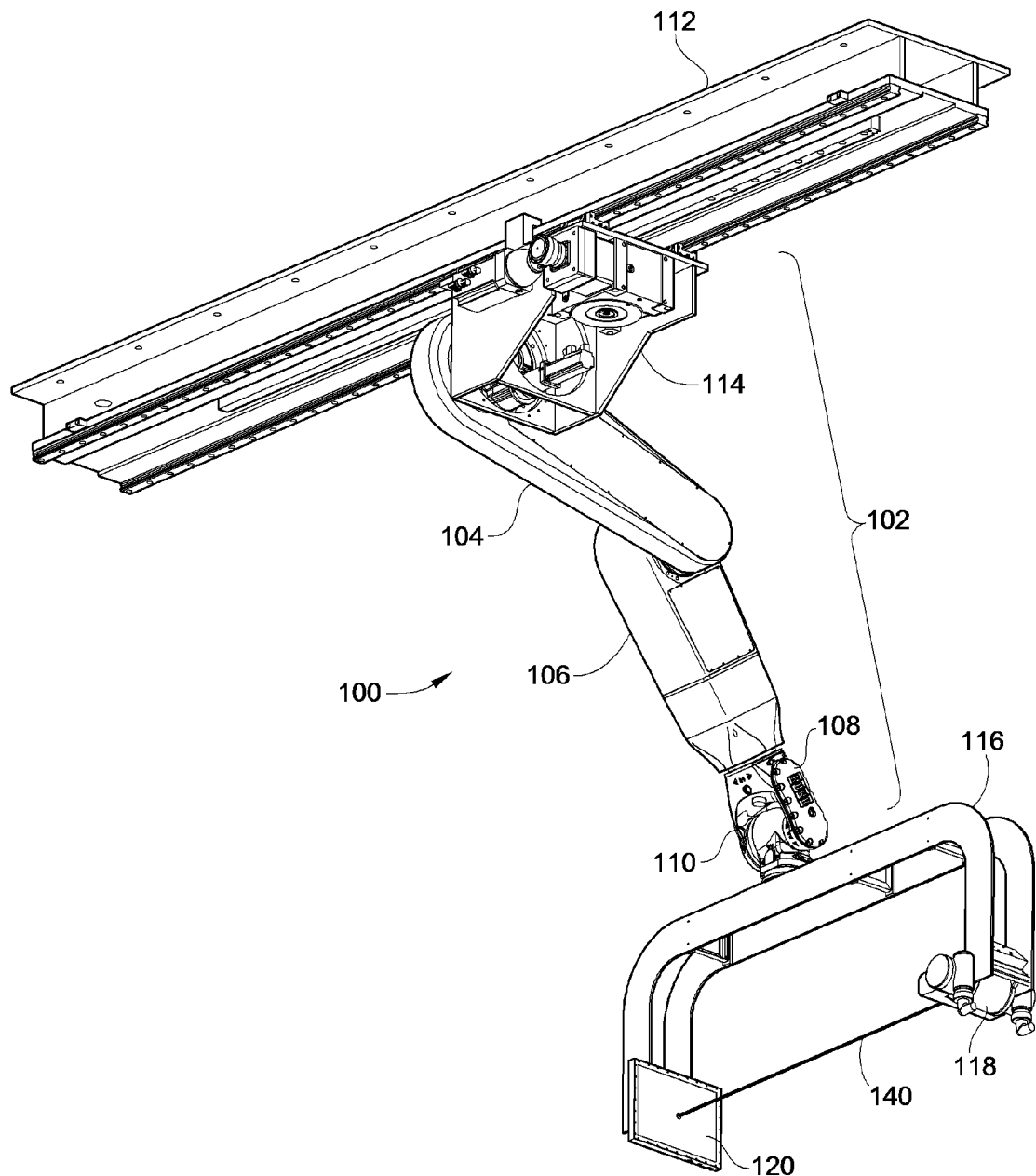
FIG. 3 is an isometric illustration of the imaging positioning system of the embodiment illustrated in FIG. 2 reoriented to illustrate additional features thereof.

FIG. 3 illustrates the same embodiment of the imaging positioning system 100 illustrated in FIG. 2, but rotated so that details of the base portion 114 and mounting track may be visible. The base portion 114 (portions of which have been removed for clarity of illustration) provides precise linear movement along mounting track 112. In one embodiment this mounting track 112 is positioned within the treatment room ceiling perpendicular to the beam treatment plane. This allows the robot 102 to approach the patient with the D-arm structure 116 from either direction to allow image acquisition in multiple planes.

Figure 4:
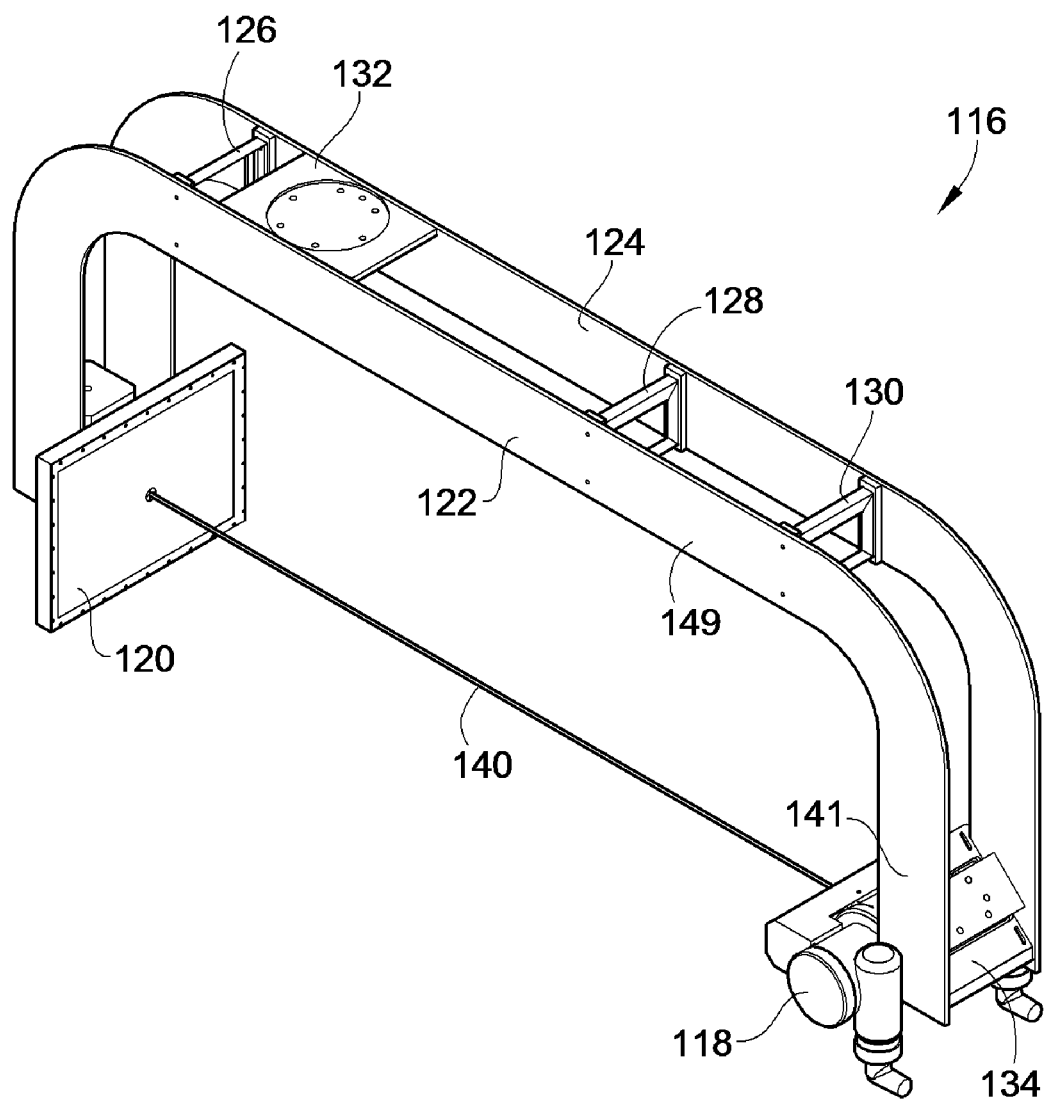
FIG. 4 is an isometric illustration of an embodiment of the D-arm utilized with the imaging positioning system of the embodiment of FIG. 1 configured to perform x-ray imaging.

The D-arm structure 116 is illustrated in greater detail in FIG. 4 to which reference is now made. In this embodiment of the D-arm structure 116, a pair of frame members 122, 124 are joined by cross braces 126, 128, 130. Mounting structure 132 is also joined to each of frame members 122, 124 and provides a mounting coupling point for the coupling portion 110 of the SCARA robot 102 (see FIG. 2). This coupling may be a rigid coupling such as may be provided by bolts or other appropriate fasteners, or may be a dynamic, releaseable coupling such as may be provided by a pneumatic coupling known in the art. A dynamic, releasable coupling would act as a uniform tool changing coupling that would shall allow for the SCARA robot 102 to be easily and automatically coupled to and uncoupled from other imaging systems, such as illustrated in FIG. 11-14.

Figure 8:
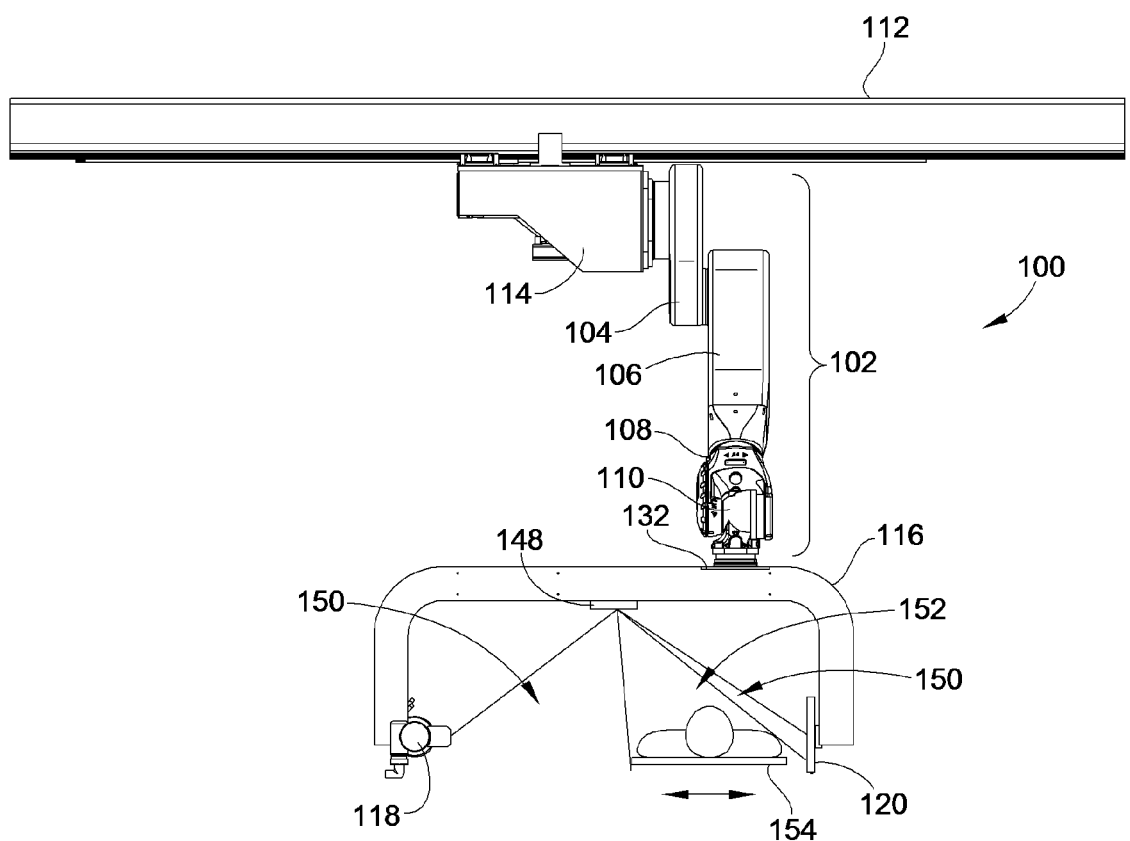
FIGS. 8-10 are front view illustration of an alternate embodiment of the imagining positioning system of the present invention illustrating the ability for the support structure to move relative to the robotic arm.
Figure 9:
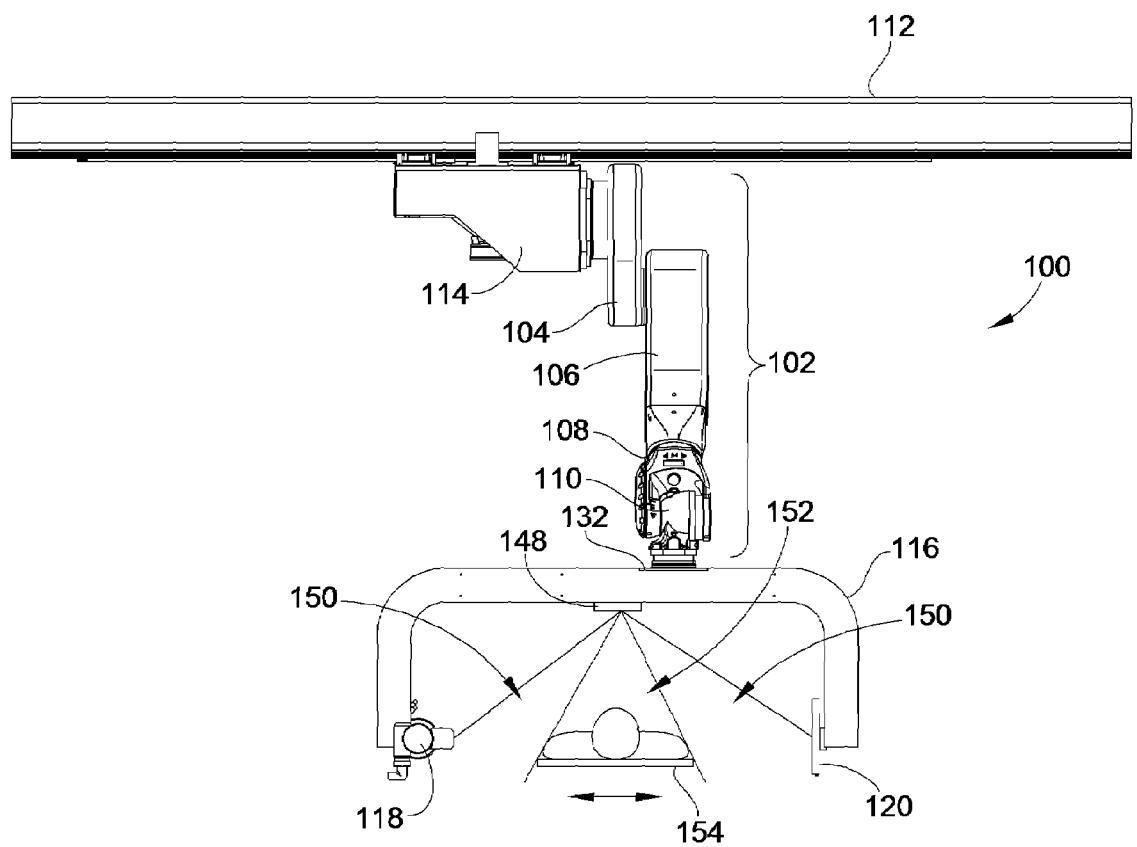
Figure 10:
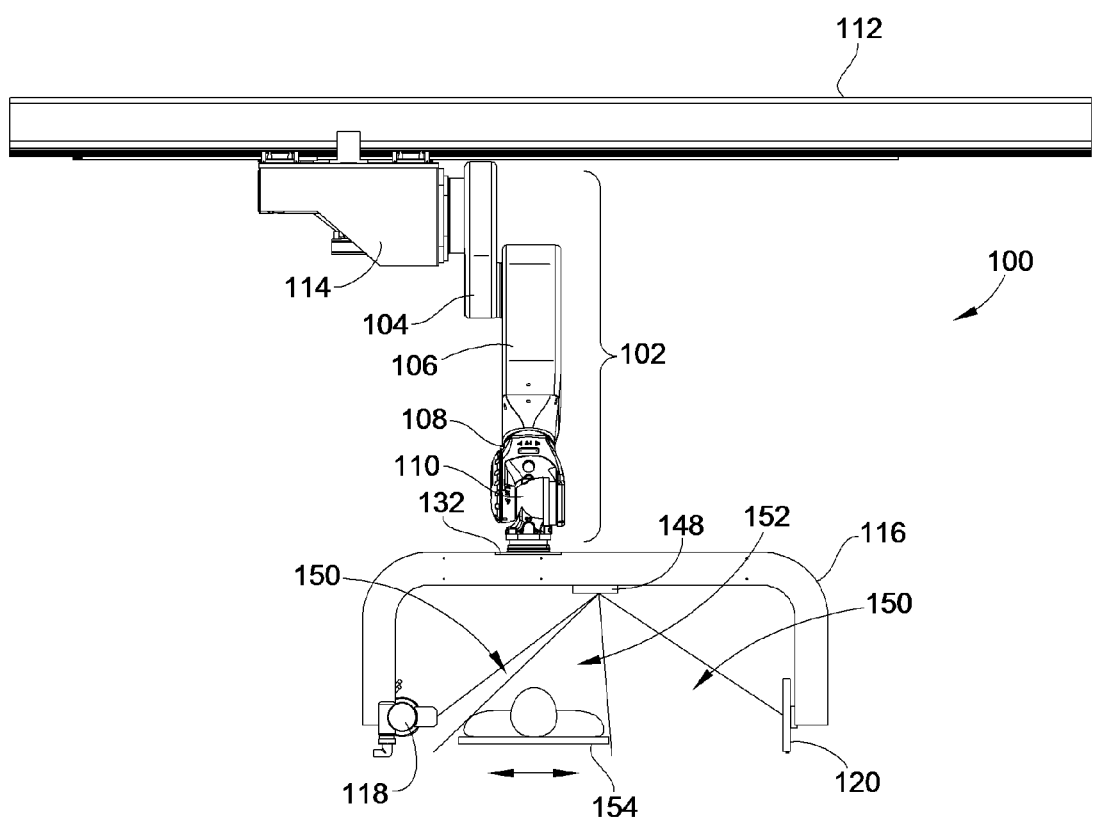

Further, as illustrated in FIGS. 8-10, the D-arm structure 116 may be mounted to the SCARA robot 102 for linear movement relative to coupling portion 110. More particularly, mounting plate 132 can move linearly about D-arm structure 116. In other words, the mounting or coupling plate 132 can move laterally between the leg portions of the D-arm and those laterally relative to x-ray source 118 and imaging panel 120. Thus, as illustrated by the progression of FIGS. 8-10, once positioned over a patient 154, the D-arm structure 116 can be moved laterally relative to SCARA robot 102 such that the patient 154 is closer to the x-ray imaging panel 120 than to the x-ray source 118 (FIG. 8), the patient 154 is substantially equally positioned between the x-ray source 118 and the x-ray imaging panel 120 (FIG. 9), or the patient 154 is closer to the x-ray source 118 than to the x-ray imaging panel 120 (FIG. 10). It should be noted that this linear translation of the D-arm structure 116 in one embodiment can be done without any movement of the SCARA robot 102 relative to the patient 154.

In one embodiment, the mounting plate 132 is moveable relative to frame members 122, 124 to laterally position the D-arm structure 116 relative to the SCARA robot 102. This allows for adjusting the orientation of the D-arm structure 116 and consequently the imaging device relative to the coupling between the D-arm and the SCARA robot 102. The mounting plate 132 may be driven by a linear actuator (not shown) to position the mounting plate 132 relative to the frame members 122, 124.

In alternative embodiments, particularly where the D-arm structure 116 is not moveable relative to the SCARA robot 102, the D-arm 116 may be mounted in an offset position relative to coupling portion 110 of the SCARA robot 102, such as illustrated by the FIGS. 2 and 9 and the position of mounting plate 132 in FIG. 4. This offset configuration is provided by having mounting plate 132 positioned laterally closer to x-ray imaging panel 120 rather than x-ray source 118.

A mounting bracket 134 is also provided between frame members 122, 124 at one end thereof for mounting the x-ray source 118 thereon. This mounting bracket 134, as well as a mounting bracket (not shown) on the other end of frame members 122, 124 for mounting of the imaging panel 120 also provides structural support and adds rigidity to the D-arm structure 116.

Figure 5:
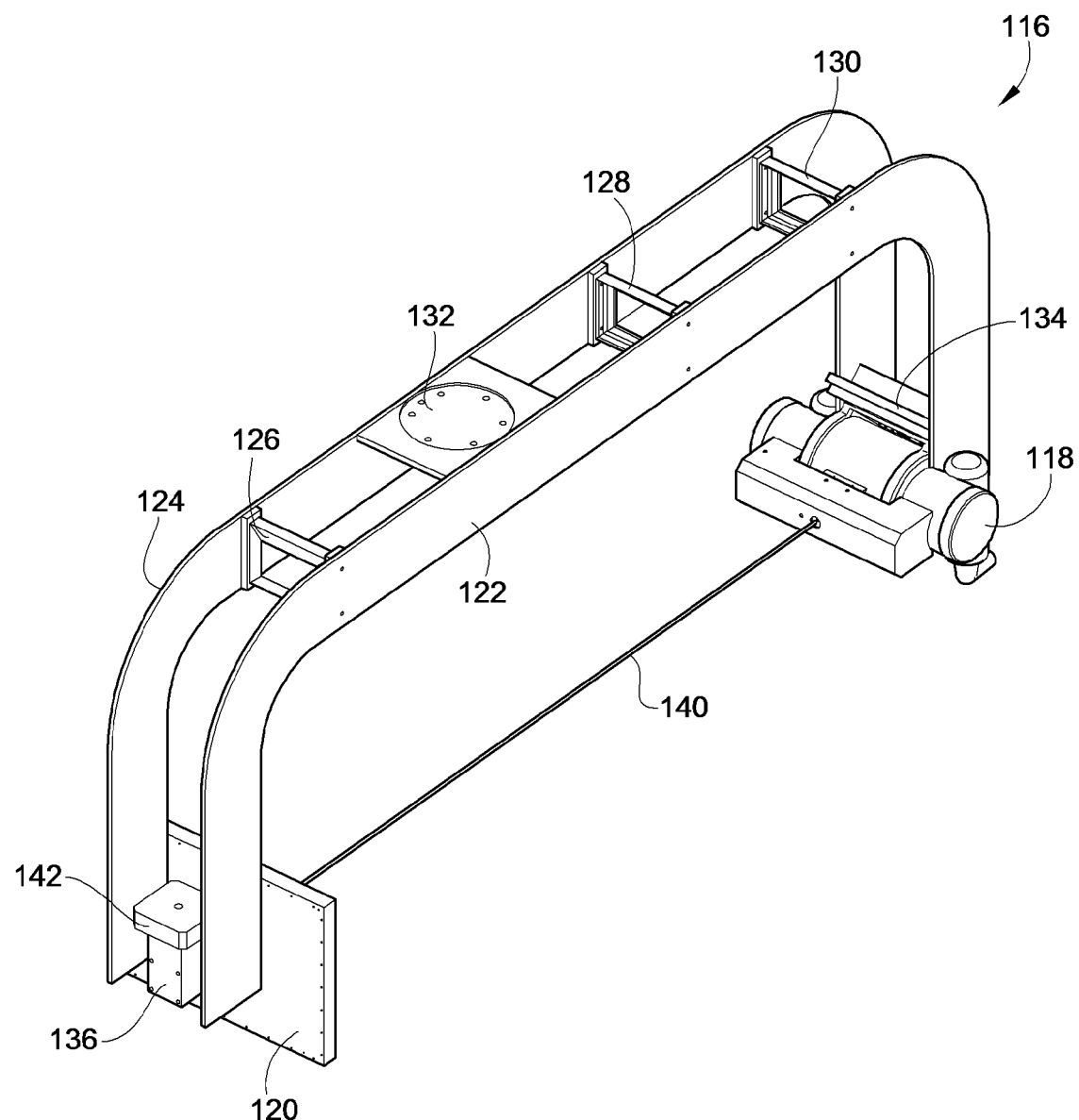
FIG. 5 is an isometric illustration of the D-arm illustrated in FIG. 4 reoriented to illustrate additional features thereof.
Figure 6:
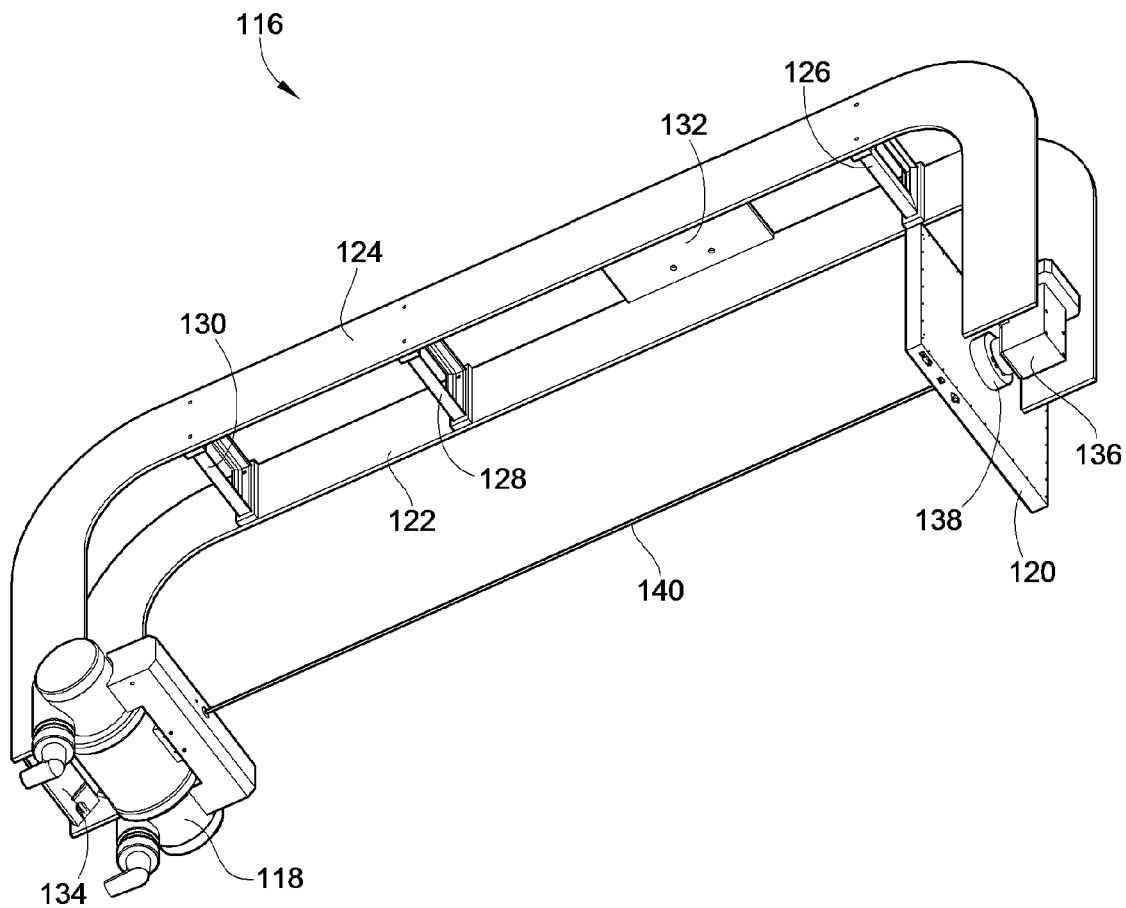
FIG. 6 is an isometric illustration of the D-arm of FIG. 4 reoriented to illustrate additional features thereof.

As may be seen in FIGS. 5 and 6 (in which the mounting bracket has been removed), the imaging panel 120 in the illustrated embodiment is not mounted directly to either of frame members 122, 124, but instead is mounted to a motor 136. As illustrated in FIG. 6, imaging panel 120 is actually mounted to a mounting structure 138 that is coupled to the output shaft of motor 136. This allows rotation of the imaging panel 120 on the D-arm structure 116. Specifically, motor 136 is able to rotate imaging panel 120 about the x-ray beam axis illustrated by line 140.

This allows the imaging system 100 to simulate a gantry rotation when a fixed proton beam that cannot rotate is used during the therapeutic operation. The classical way of using static radiographic images is to have the imaging panels in a fixed orientation with respect to the fixed reference coordinate system in the treatment room. When the patient is moved, instead of the beam (gantry) and the radiographic image is obtained with the prior fixed panel, the image will not align with the reference image obtained from the treatment planning system. In this embodiment of the present invention, this problem is solved by rotating the imaging panel 120 about the x-ray axis 140 to simulate the effect of a beam rotation.

In embodiments that utilize rigid frame members 122, 124 and that fix the imaging panel 120 and the x-ray source 118 along the x-ray beam axis 140, it is impossible to use the same imaging panel 120 for a beam line x-ray image in a treatment center. This is because such imaging requires the imaging panel be positioned perpendicular with the proton beam axis, and with a fix mount of the x-ray source 118 and the imaging panel 120 on the D-arm structure 116 the x-ray source 118 will collide with the beam delivery nozzle of the treatment beam when the imaging panel is moved into proper position.

However, in an embodiment of the present invention the image panel mount 142 will allow the imaging panel 120 to tilt out of the plane of the x-ray beam axis 140 so that the imaging panel 120 can be positioned perpendicular to the proton beam axis without the x-ray source 118 hitting the beam delivery nozzle. In one embodiment to the present invention the image panel mount 142 will only need to provide a tilt angle of less than approximately 45 degrees, and preferably approximately 30 degrees out of the x-ray beam axis 140. This will allow adequate clearance between the x-ray source 118 and the beam delivery nozzle of the proton beam treatment device when the imaging panel 120 is positioned perpendicular to the proton beam axis, thereby allowing the beam line x-ray image to be taken.

Figure 7:
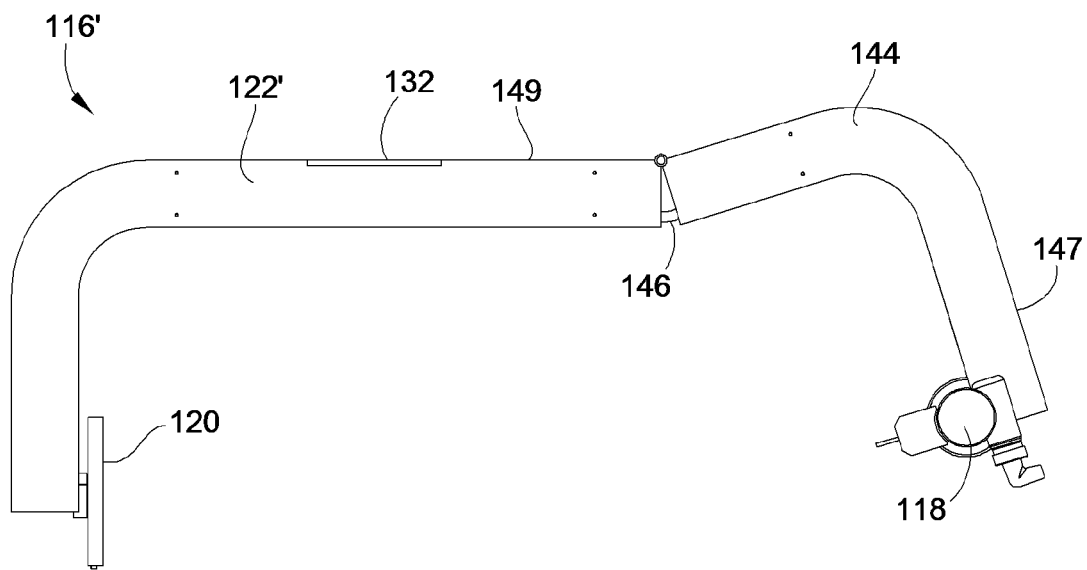
FIG. 7 is a side view illustration of an alternate embodiment of a D-arm configured for x-ray imaging and beam line x-ray imaging.

In an alternate embodiment of the D-arm structure 116' illustrated in FIG. 7, the frame members 122' include a hinged portion 144 and a drive mechanism 146. In this embodiment the x-ray source 118 is able to be rotated out of the way of the ion beam delivery nozzle when the imaging panel 120 is positioned perpendicular to the proton beam axis. This will then allow beam line x-ray imaging using the imaging panel 120 while avoiding a collision between the x-ray source 118 and the beam delivery nozzle. Again, this is another structural arrangement that permits adjustment of the orientation of the imaging device relative to the coupling between the SCARA robot 102 and the D-arm structure 116.

While FIG. 7 clearly shows that the mounting arrangement of the x-ray source 118 and x-ray imaging panel 120 allows for the x-ray source 18 to be rotated out of line with the x-ray imaging panel 120 to allow beam line x-ray imaging to use the imaging panel 120, alternative embodiments of the invention are not limited to this location of the hinge or pivot point for rotating the x-ray source 118 out of alignment with imaging panel 120. For example and with reference to FIG. 4, the x-ray source 118 may pivot relative to the arm portion 147 that extend perpendicularly to arm portion 149 of the D-arm structure 116 to which the x-ray source 118 is mounted.

The imaging positioning system 100 of the present invention will not only allow the acquisition of static x-ray images along multiple axis through the treatment room isocenter, but will also allow for cone beam CT acquisition. These CBCT acquisitions are achieved by controlling the SCARA robot 102 to dynamically rotate the D-arm structure 116 about the patient in multiple planes. Further, because the SCARA type robot 102 is used to position and rotate the D-arm structure 116, a dynamic field of view (FOV) for the CBCT acquisitions is possible. That is, since the center of rotation between the x-ray source 118 and the imaging panel 120 for CBCT acquisitions are determined by the SCARA robot 102, the technician or medical personnel may define a point of rotation that will control the FOV. If a larger FOV is required, the point of rotation of the D-arm structure 116 about the patient may be user defined to be closer to the imaging panel 120. If a smaller FOV is required, the point of rotation of the D-arm structure 116 about the patient may be user defined to be closer to the x-ray source 118 and farther from the imaging panel 120. Typical CBCT systems, to the contrary, rotate about a fixed point in space. As such, their FOV is also fixed.

A further advantage of the system 100 of the present invention is that CBCT acquisitions may be obtained while the patient is in the treatment position. That is, because the SCARA robot 102 can dynamically position the D-arm structure 116 to provide CBCT acquisitions in multiple planes, such CBCT acquisitions may be done in the treatment position. Still further, these CBCT acquisitions may be performed with the patient in a seated, i.e. upright, position. This is made available in the system of the present invention because the SCARA robot 120 can dynamically position the D-arm structure 116 to acquire a CBCT in the horizontal plane.

As discussed briefly above, positron emission tomography (PET) cameras may be mounted in place of the x-ray source 118 and the imaging panel 120, or may be mounted to the D-arm structure 116 in addition to or in place of the x-ray source 118 and imaging panel 120. Because the SCARA robot 102 can dynamically position the D-arm structure 116 within the treatment room while the patient is being actively treated, PET imaging can be performed in the treatment room without moving the patient into a separate PET scanner. This is made possible by the D-arm structure 116 by positioning the PET cameras at diametrically opposed positions thereon. This is required because during the annihilation process, two photons are emitted in diametrically opposing directions. These photons are registered by the PET cameras as soon as they arrive and the data is forwarded to a processing unit which decides if the two registered events are selected as a so-called coincidence event. All such coincidences are forwarded to an image processing unit where the final image data is produced via image reconstruction procedure well known in the PET scanning art.

In an embodiment of the present invention as illustrated in FIGS. 8-10, a laser distance tracking device, such as a laser scanner 148, is mounted on the D-arm structure 116. This laser scanner 148 will sweep over the volume 150 enclosed by the D-arm structure 116. The laser scanner 148 will sense the presence of any objects that come in close proximity of any mechanical part of the D-arm structure 116 within volume 150. The SCARA robot control will receive the scanner data so as to control the position of the D-arm structure 116 to prevent objects from coming in close proximity or contact with any mechanical part on the D-arm structure 116. The output data from the laser scanner may also be exported to a patient positioning system collision avoidance algorithm. In such an embodiment, the laser scanner 148 of the imaging system 100 will scan over the patient 154 prior to the start of a treatment to determine the envelope 152 occupied by the patient 154. Once this envelope 152 has been determined, the patient positioning system's collision avoidance algorithm will ensure that no object is allowed to enter the envelope 152 during the treatment process.

In one embodiment of the present invention the coupling portion 110 of the SCARA robot 102 will include a force torque sensor. In such an embodiment, all motions of the SCARA robot 102 and the D-arm structure 116 will be under force torque control, except for dynamic CBCT acquisitions. In such an embodiment none of the motions about the patient to position to the D-arm structure 116 in position will be autonomous. Instead, positioning of the D-arm structure 116 by the SCARA robot 102 will be controlled by a user pulling the D-arm structure 116 into position.

Figure 11:
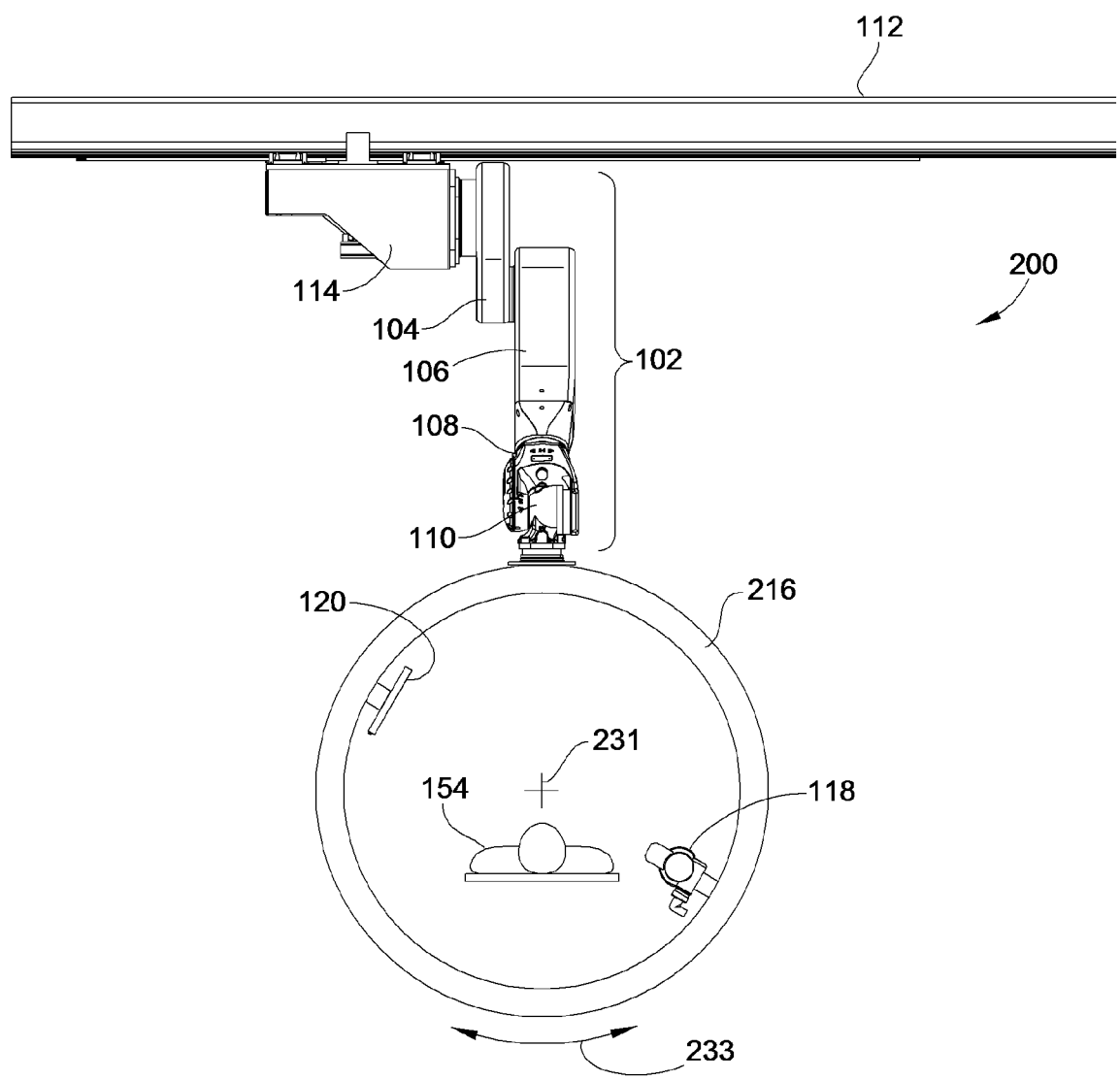
FIGS. 11-14 illustrate an alternative embodiment of an imaging positioning system that utilizes a support ring for supporting the imaging components of the system.

With reference to FIG. 11, an alternative embodiment of an imaging positioning system 200 is illustrated. The imaging positioning system 200 is similar to the prior imaging positioning systems described previously in many respects. For example, the imaging positioning system 200 incorporates a SCARA robot 102 for robotically positioning another embodiment of a support structure for carrying and positioning imaging equipment.

In this embodiment, the support structure is support ring 216 that forms a continuous ring that surrounds an entire 360° for providing additional positioning configurations of x-ray source 118 and x-ray imaging panel 120 relative to a patient 154. While illustrated as a circular support ring 216, support ring 216 is intended to be broad enough to encompass other annular or ring-type structures that may be polygonal in shape, oblong, elliptical, oval, etc. while still substantially forming a ring. Further, the ring need not necessarily form or be able to form an entire continuous ring.

Figure 12:
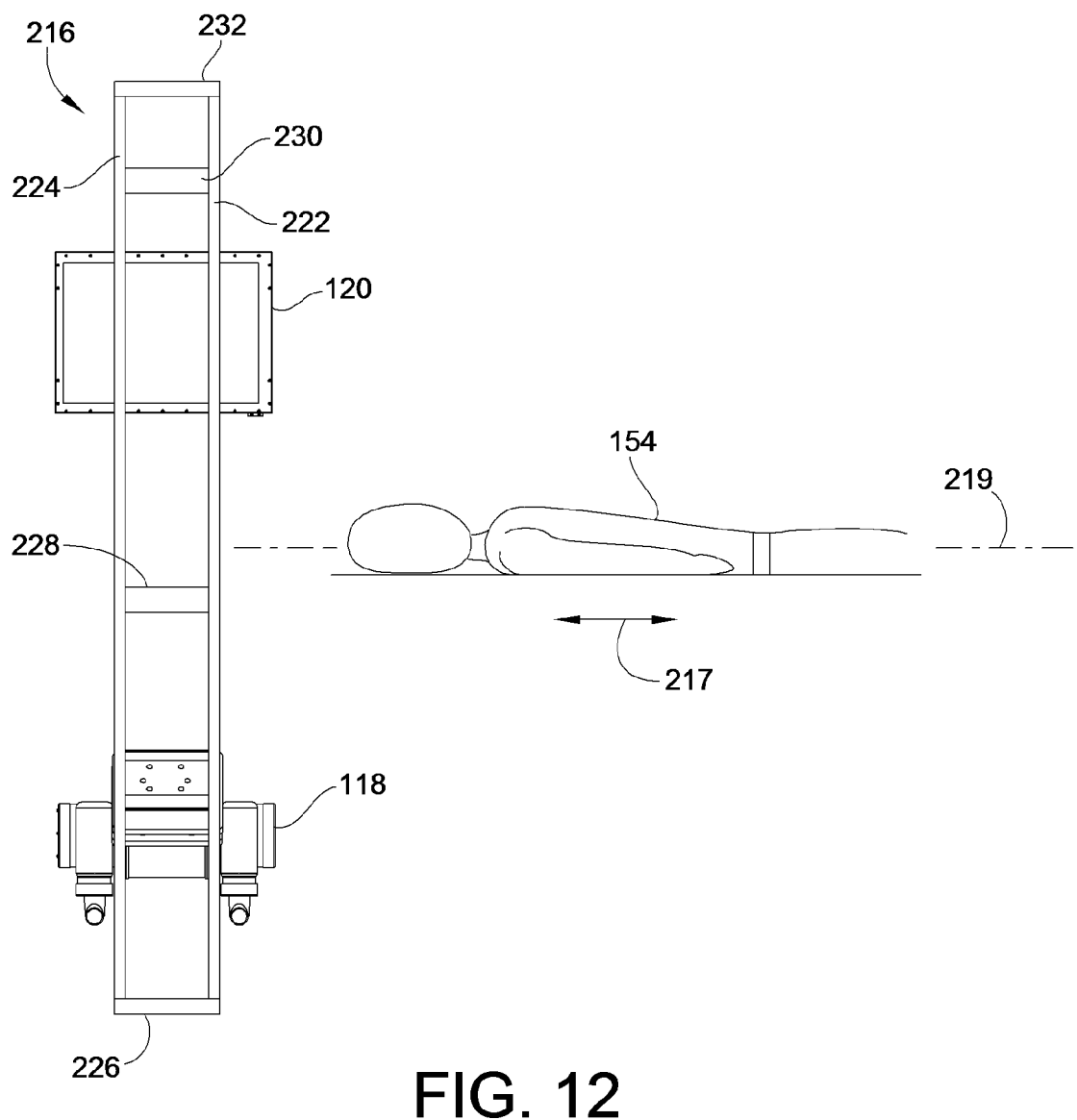

The illustrated support ring 216 in FIGS. 11 and 12 forms a continuous fixed ring. As it is a continuous ring, the support ring 216 must be positioned (illustrated by double arrows 217) relative to the patient 154 by moving along a path 219

(illustrated as a dashed line) defined by the patient 154. As illustrated in FIG. 12, the patient 154 is laying on a flat support such as a couch or a bed such that path 219 is substantially linear. Thus, the support ring 216 can be moved linearly along path 216 so as to take x-ray images of desired locations of patient 154.

The illustrated support ring 216 is similar to the D-arm structure 116 of the previous embodiments, in that it is formed from a pair of frame members 222, 224 that are spaced apart from and connected to one another by cross-braces 226, 228, 230. Further, the x-ray source 118 and x-ray imaging panel 120 can be mounted to the support ring 216 in identical fashion as in the embodiments described previously with regard to the D-arm structure 116. Additionally, the support ring 216 may include a mounting structure 232 similar to mounting structure 132 of previous embodiments.

In one embodiment of the imaging positioning system 200 of FIGS. 11 and 12, the support ring 216 can rotate, typically via mounting structure 232, about an axis of rotation 231 relative to coupling portion 110. This additional degree of freedom, allows the x-ray source 118 and x-ray imaging panel 120 to be rotated about the patient 154 to vary the angle at which x-ray images are taken of the patient 154. This degree of freedom is preferably an entire 360° about axis 231 and preferably permitted in either a clockwise or counter-clockwise direction about axis 231 (i.e. as illustrated by double arrow 233 in FIG. 11). More particularly, this allows the x-ray source 118 and x-ray imaging panel 120 to take x-rays from substantially any direction along or parallel to a plane defined by axis of rotation 231.

Figure 13:
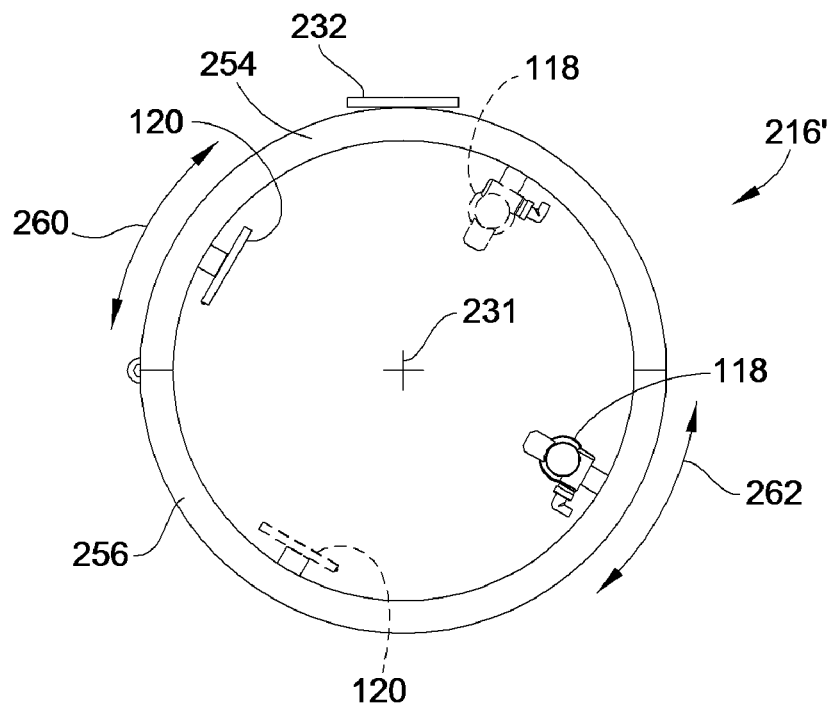
Figure 14:
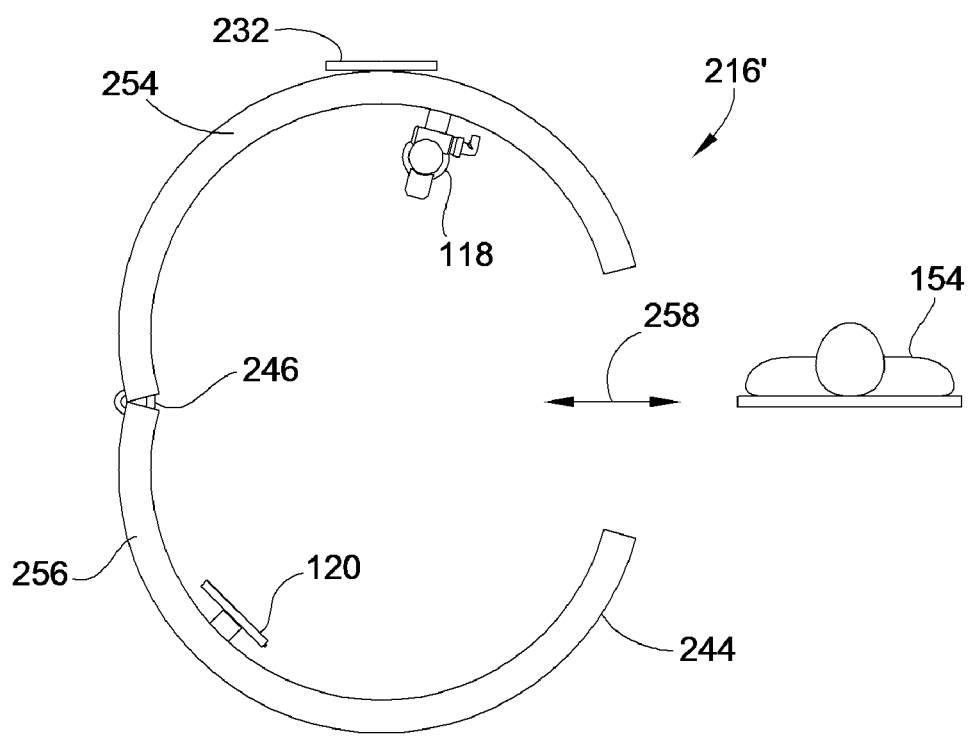

A further embodiment of a support ring 216' is illustrated in FIGS. 13 and 14. Support ring 216' is similar to support ring 216 except that the support ring 216' is formed by a pair of ring portions 254, 256, i.e. segments, that pivot relative to one another between first and second pivotal states. Ring portion 256 acts as a hinged portion that pivots relative to ring portion 254. A drive mechanism 246 drives the two portions 254, 256 relative to one another to open and close the support ring 216'. In the open pivotal state (see FIG. 14), a mouth is formed between the distal ends of the ring portions 254, 256.

This configuration allows for more easily positioning the support ring 216' relative to a patient. Instead of being required to move along an axis defined by a patient and passing over the head or feet of the patient first, this clam version of the support ring 216' can be opened (as illustrated in FIG. 14) such that it can be directly positioned laterally about a patient 154 illustrated by double arrow 258, such as at the waist of the patient 154, rather than over the feet or head first.

A further feature of using a support ring design such as support rings 216, 216' is that the x-ray source 118 and x-ray imaging panel 120 can move relative to support rings 216, 216' such that the components move about the circumference defined by the support rings and axis 231 without the support ring 216, 216' itself having to be moved relative to SCARA robot 102. This ability to move only the x-ray source 118 and x-ray imaging panel 120 relative to support ring 216, 216' can improve precision of the positioning of the imaging system while reducing the strength of any motor used to rotate the imaging system. More particularly, rather than being required to rotate the entire load and over come the angular inertia of support ring 216, 216' combined with the x-ray source 118 and x-ray imaging panel 120, only the x-ray source 118 and x-ray imaging panel 120 relative to axis 231 must be moved.

FIG. 13 illustrates the ability to move the x-ray source 118 and x-ray imaging panel 120 relative to support ring 216'. In a preferable embodiment, x-ray source 118 and x-ray imaging panel 120 relative to support ring 216' in both forward and reverse directions, such as illustrated by double arrows 260, 262 as well as the dashed representations of x-ray source 118 and x-ray imaging panel 120.

Further, in one embodiment, the x-ray source 118 and x-ray imaging panel 120 may be positioned relative to support ring 216, 216' independently from one another such that the two devices can move toward one another (typically, they will be positioned along a diameter of the support ring 216, 216' such that they are equally spaced in either the clockwise or counter-clockwise directions). This can be beneficial in the situation where it is desired to use the x-ray imaging panel 120 in conjunction with beam line x-ray imaging to align the therapeutic radiation beam.

Alternatively, in another embodiment, the movement of the x-ray source 118 and x-ray imaging panel 120 may be coordinated such that they both move simultaneously about axis 231 the same amount such that they relative positions of the two devices remains the same.

Thus, the use of a support ring 216, 216' provides substantial improvements in positioning of the imaging positioning devices relative to a patient for improved precision and usability. Further, as the SCARA robot 102 is not required to do fine angular positioning of the entire support structure 116, 116', 216, 216', the x-ray source 118 and the x-ray imaging panel 120, the overall strength and power of the SCARA robot 102 can be reduced while increasing the positioning sensitivity of the imaging system.

It should be noted that all of the control and safety features for the D-arm structure 116 embodiments can be incorporated with the support ring 116 embodiments All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An imaging positioning system, comprising:
   a support structure;
   an imaging device positioned on the support structure;
   a robotic arm coupled to the support structure at a coupling between the support structure and the robotic arm, the robotic arm operative to move the support structure along multiple rotational axes and at least one linear axis;
   wherein the orientation of the imaging device relative to the coupling is adjustable;
   wherein the position of the coupling is adjustable relative to support structure, thereby allowing adjustability of the orientation of the imaging device relative to the coupling; and
   wherein the coupling includes a coupling plate that is moveable along and relative to the support structure.

2. The imaging positing system of claim 1, wherein the imaging device is moveable along the support structure, thereby allowing adjustability of the orientation of the imaging device relative to the coupling.

3. The imaging positioning system of claim 2, wherein the support structure is a ring structure formed by at least two segments that pivot relative to one another to make a continuous ring in a first pivoted state and to break the continuous ring in a second pivoted state forming an opening between the two segments in the second pivoted state.

4. The imagining positioning system of claim 2, wherein the support structure is a ring structure and the imaging device is movable relative to the ring structure about the entire circumference defined by the ring structure.

5. The imaging device of claim 2, wherein the position of the coupling is adjustable relative to the support structure.

6. The imaging device of claim 1, wherein the imaging device includes two separate imaging components, each component operatively mounted to the support structure, the two imaging components are pivotable relative to each other.

7. The imaging device of claim 6, wherein the support structure is segmented into two portions that are pivotally connected to one another for relative angular movement therebetween, one component is operatively mounted to one of the portions and the other one of the components being operatively mounted to the other one of the portions, the two components pivotable relative to each other via the pivotal connection between the two support structure segments.

8. The imaging device of claim 7, wherein the support structure has a concave profile open on one side for receipt of a patient therethrough for positioning the patient between the two imaging components.

9. The imaging device of claim 6, wherein at least one of the two imaging components is pivotally mounted to the support structure such that pivotally mounted imaging component can be pivoted out of alignment with the other one of the imaging components without adjusting an orientation or a configuration of the support structure.

10. The imaging device of claim 6, wherein the coupling between the support structure and the robotic arm is positioned closer to one of the imaging components than the other one of the imaging components.

11. The imaging device of claim 1, further including a force torque sensor and the robotic arm is operably configured such that positioning of the support structure is controllable by pulling on the support structure and is not autonomously controlled by the robotic arm.

12. The imaging device of claim 1, further including a laser distance tracking device, the laser distance tracking device configured to sweep the volume defined by the support structure and configured to sense the presence of any objects within the volume defined by the support structure.

13. The imaging device of claim 12, wherein the laser distance tracking device further configured to determine an envelope defined by a patient positioned within the volume defined by the support structure, the imaging device being configured to prevent any portion of the imaging device from entering the envelope defined by the patient.

14. The imaging device of claim 13, wherein the laser distance tracking device includes a laser scanner and a control including a patient positioning system collision avoidance algorithm that takes the data from the laser scanner and ensure that no object of the imaging device is allowed to enter the envelope defined by the patient.

15. An imaging positioning system, comprising:
   a support structure;
   an imaging device positioned on the support structure; and
   a robotic arm coupled to the support structure at a coupling between the support structure and the robotic arm, the robotic arm operative to move the support structure along multiple rotational axes and at least one linear axis;
   wherein the coupling between the support structure and the robotic arm is a uniform tool changing coupling such that the support structure can be automatically released from and coupled to the robotic arm.

16. The imaging positioning system of claim 15, further comprising an auxiliary support structure independent from the support structure, the auxiliary support structure and robotic arm forming an auxiliary coupling therebetween, the auxiliary coupling between the auxiliary support structure and the robot arm is a uniform tool changing coupling such that the auxiliary support structure can be automatically released from and coupled to the robotic arm using the same coupling structure that robotic arm uses to form the coupling with the support structure.

* * * * *